United States Patent [19]

Orth et al.

[11] 4,188,403

[45] Feb. 12, 1980

[54] CYCLOPENTAN-1-AMINES

[75] Inventors: Dieter Orth; Hans-Eckart Radunz; Manfred Baumgarth; Jürgen Maisenbacher; Reinhard Lissner, all of Darmstadt, Fed. Rep. of Germany

[73] Assignee: Merck Patent Gesellschaft mit beschränkter Haftung, Darmstadt, Fed. Rep. of Germany

[21] Appl. No.: 863,001

[22] Filed: Dec. 21, 1977

[30] Foreign Application Priority Data

Dec. 23, 1976 [DE] Fed. Rep. of Germany ....... 2658401

[51] Int. Cl.² ................ A61K 31/135; C07C 91/16
[52] U.S. Cl. ................ 424/330; 260/563 R; 260/570.5 CA; 424/309; 424/325; 424/300; 424/319; 424/305; 560/27; 560/43; 560/115; 560/121; 562/452; 562/503
[58] Field of Search ............... 260/563 R, 570.5 CA; 424/325, 330

[56] References Cited

U.S. PATENT DOCUMENTS 3,896,171  7/1975  Holtschmidt et al. .............. 424/325

Primary Examiner—Bernard Helfin
Assistant Examiner—G. T. Breytenstein
Attorney, Agent, or Firm—Millen & White

[57] ABSTRACT

Compounds of the Formula

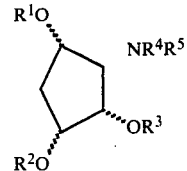

and the physiologically acceptable salts thereof, wherein $R^1$ and $R_2$ each is hydrogen or benzyl; $R^3$ is alkyl of 5–10 C-atoms or 2-hydroxyalkyl of 5–10 C-atoms; $R^4$ is hydrogen, methyl or ethyl; $R^5$ is alkyl of 5–10 C-atoms or $-C_nH_{2n}COOR^6$; $R^6$ is hydrogen or alkyl of 1–4 C-atoms; and n is 0, 4, 5 or 6 are effective for inhibiting adhesion and/or agglomeration of thrombocytes.

20 Claims, No Drawings

CYCLOPENTAN-1-AMINES

SUMMARY OF THE INVENTION

It is an object of the present invention to provide new compounds which, in particular, can be used advantageously for the preparation of medicaments, especially for use in thrombocyte aggregation and adhesion inhibition.

Upon further study of the specification and appended claims, further objects and advantages of this invention will become apparent to those skilled in the art.

These objects have been obtained by providing, in a composition aspect, cyclopentan-1-amines of Formula I

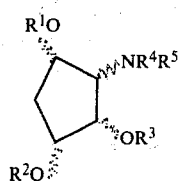

and the physiologically acceptable salts thereof, wherein $R^1$ and $R^2$ each is hydrogen or benzyl; $R^3$ is alkyl of 5–10 C-atoms or 2-hydroxyalkyl of 5–10 C-atoms; $R^4$ is hydrogen, methyl or ethyl; $R^5$ is alkyl of 5–10 C-atoms or $-C_nH_{2n}COOR^6$; $R^6$ is hydrogen or alkyl of 1–4 C-atoms; and n is 0, 4, 5 or 6. A wavy line indicates that the bond can be in the α- or β-position. In a second composition aspect, the present invention provides a pharmaceutical composition comprising an amount of a compound of Formula I effective to inhibit aggregation and/or adhesion of thrombocytes and a pharmaceutically acceptable carrier.

In a method of use aspect, the present invention provides a method of inhibiting aggregation and/or adhesion of thrombocytes in mammals, including humans, which comprises administering an amount of a compound of Formula I effective for such inhibition.

DETAILED DISCUSSION

In Formula I and the other formulae herein, an α-position bond is indicated by a dotted line and a β-position bond by an unbroken line. Bonds which may be in the α- or β-position are indicated by a wavy line.

The compounds of Formula I contain 4 asymmetrical C-atoms in the five-membered ring. However, additional centers of asymmetry can occur, for example, when $R^3$ is a branched alkyl radical of 5–10 C-atoms or 2-hydroxyalkyl of 5–10 C-atoms, or when $R^5$ is a branched alkyl of 5–10 C-atoms or branched $-C_nH_{2n}COOR^6$. The compounds of Formula I can, therefore, occur in a plurality of stereoisomeric forms. As a rule, they are present as racemic mixtures, together with their mirror images.

The compounds of Formula I, and the physiologically acceptable salts thereof, in which $-OR^3$ and $-NR^4R^5$ are located trans to one another, especially in which $OR^3$ is in the α-position and $-NR^4R^5$ in the β-position are preferred, as in Formula Ia:

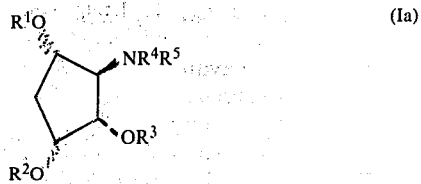

Of this class of compounds of Formula Ia those are especially preferred in which $R^1O$ and $R^2O$ are both cis to $OR^3$ especially also in the α-position, as in Formula Ib:

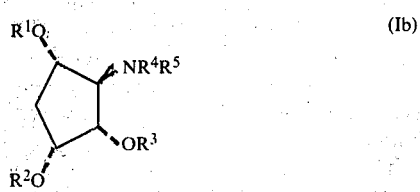

Besides individual racemates and racemic mixtures, the present invention also includes the optically-active isomers of the compounds of Formula I, especially also of formulae Ia and Ib, as well as their mirror images and the physiologically acceptable salts thereof.

$R^1$ and $R^2$ are preferably the same but can also be different and each is hydrogen or especially benzyl.

$R^3$ preferably is an alkyl radical of 5–10 C-atoms, especially one which is unbranched, such as pentyl, octyl, nonyl, decyl and, especially, heptyl. Branched radicals are also suitable. Of the branched alkyl radicals of 5–10 C-atoms, preferred radicals include: 1-methylbutyl, 1-methylpentyl, 2-methylpentyl, 3-methylpentyl, 1-methylhexyl, 2-methylhexyl, 3-methylhexyl, 1-methylheptyl, 2-methylheptyl, 3-methylheptyl, 6-methylheptyl, 3,3-dimethylheptyl, 6,6-dimethylheptyl, 2-ethylheptyl, 3-ethylheptyl, 1-methyloctyl, 2-methyloctyl, 3-methyloctyl, 1-methylnonyl, 2-methylnonyl and 3-methylnonyl. Especially preferred are those radicals which contain 7 C-atoms in the longest chain.

$R^3$ can also be 2-hydroxyalkyl of 5–10 C-atoms. Those radicals which are unbranched or only contain a methyl branching in the 2-position are preferred, e.g., 2-hydroxypentyl, 2-hydroxyhexyl, 2-hydroxyoctyl, 2-hydroxynonyl, 2-hydroxydecyl, 2-hydroxy-2-methylbutyl, 2-hydroxy-2-methylpentyl, 2-hydroxy-2-methylhexyl, 2-hydroxy-2-methyloctyl, 2-hydroxy-2-methylnonyl and especially 2-hydroxyheptyl and 2-hydroxy-2-methylheptyl.

Other suitable 2-hydroxyalkyl radicals of 5–10 C-atoms include: 2-hydroxy-1-methylheptyl, 2-hydroxy-1,2-dimethylheptyl, 2-hydroxy-2,3-dimethylheptyl, 2-hydroxy-3,3-dimethylheptyl, 2-hydroxy-6,6-dimethylheptyl, 2-hydroxy-2,3,3-trimethylheptyl, 2-hydroxy-1-methylhexyl, 2-hydroxy-1-methyloctyl and 2-hydroxy-1-methylnonyl.

$R^4$ can be hydrogen or ethyl, and preferably methyl.

$R^5$ is either alkyl of 5–10 C-atoms, of which those mentioned as preferred for $R^3$ are also preferred for $R^5$, or $-C_nH_{2n}COOR^6$. n can be 0, 4 or 6, preferably 5. When n is not 0, then $-C_nH_{2n}-$ is, in particular, a tetramethylene, hexamethylene or especially pentamethylene group. However, $-C_nH_{2n}-$ can also be a branched alkylene group of 4–6 C-atoms, such as 1-methyl-tetramethylene, 1,1-dimethyltetramethylene, 1-ethyltetramethylene and especially 1-methyl-pentamethylene, whereby the methyl group is preferably adjacent to the COOR$^6$ group.

R$^6$ is especially hydrogen but also can be alkyl of 1–4 C-atoms. The unbranched alkyl radicals are preferred, such as methyl, propyl, butyl and especially ethyl. However, branched alkyl radicals are also suitable, e.g., R$^6$ can be: isopropyl, secbutyl, isobutyl and tert-butyl. R$^6$ is also preferably tert-butyl when n=0.

Based on the preferred embodiments of n and R$^6$, R$^5$ is, therefore, in particular, also 4-hydroxycarbonylbutyl, 4-ethoxycarbonylbutyl, 6-hydroxycarbonylhexyl, 6-ethoxycarbonylhexyl, tertbutoxycarbonyl and especially 5-hydroxycarbonylpentyl and 5-ethoxycarbonylpentyl. Other preferred R$^5$ groups include: 4-methyl-4-hydroxycarbonylbutyl, 5-methyl-5-hydroxycarbonylpentyl, 5-methyl-5-ethoxycarbonylpentyl, 5-methoxycarbonylpentyl, 5-propyloxycarbonylpentyl and 5-butyloxycarbonylpentyl.

Those compounds of the Formula I are especially preferred in which at least one of the symbols R$^1$ to R$^6$ and n has one of the meanings stated above to be preferred. Some of these preferred groups of compounds can be characterised by the following partial formulae Ic to Im which otherwise correspond to Formula I and in which the symbols not more precisely defined have the meanings given above for Formula I, wherein however:

in Ic, R$^1$=R$^2$=benzyl;
in Id, R$^1$=R$^2$=H;
in Ie, R$^3$=unbranched alkyl of 5–10 C-atoms;
in If, R$^5$=unbranched alkyl of 5–10 C-atoms, —(CH$_2$)$_5$—COOH or (CH$_2$)$_5$COOC$_2$H$_5$,
in Ig, R$^1$=R$^2$=benzyl, R$^3$=unbranched alkyl of 5–10 C-atoms,
in Ih, R$^1$=R$^2$=benzyl, R$^5$=unbranched alkyl of 5–10 C-atoms, —(CH$_2$)$_5$—COOH or —(CH$_2$)$_5$COOC$_2$H$_5$,
in Ii, R$^1$=R$^2$=benzyl, R$^3$=unbranched alkyl of 5–10 C-atoms, R$^5$=unbranched alkyl of 5–10 C-atoms, —(CH$_2$)$_5$—COOH or —(CH$_2$)$_5$COOC$_2$H$_5$,
in Ij, R$^1$=R$^2$=benzyl, R$^3$=heptyl, R$^5$=unbranched alkyl of 5–10 C-atoms, —(CH$_2$)$_5$—COOH or —(CH$_2$)$_5$COOC$_2$H$_5$,
in Ik, R$^1$=R$^2$=benzyl, R$^3$=heptyl, R$^5$=heptyl, —(CH$_2$)$_5$—COOH or —(CH$_2$)$_5$—COOC$_2$H$_5$,
in Il, R$^1$=R$^2$=benzyl, R$^3$=heptyl, R$^4$=methyl, R$^5$=heptyl, —(CH$_2$)$_5$—COOH or —(CH$_2$)$_5$—COOC$_2$H$_5$,
in Im, R$^1$=R$^2$=H, R$^3$=heptyl, R$^4$=methyl, R$^5$=heptyl, —(CH$_2$)$_5$—COOH or —(CH$_2$)$_5$—C$_2$H$_5$.

In particular, those compounds of Formulae Ic to Im are preferred in which the steric relationships shown in formulae Ia and Ib are present.

The preparation of the compounds of Formula I may be accomplished by per se known methods, such as are described in the literature (e.g. in the standard works, such as Houben-Weyl, *Methoden der organischen Chemie,* Georg-Thieme-Verlag, Stuttgart; *Organic Reactions,* John Wiley & Sons, Inc., New York), i.e., under known reaction conditions suitable for such reactions. Thus, per se known variants of these processes, which are not mentioned in detail herein, can also be used. The same also applies to the preparation of the starting compounds II to XI described below, which, if desired, can also be prepared in situ, i.e., without isolation from the reaction mixture but rather using immediate additional reaction to form the compounds of Formula I.

The compounds of Formula I can be prepared by reacting a compound of Formula II

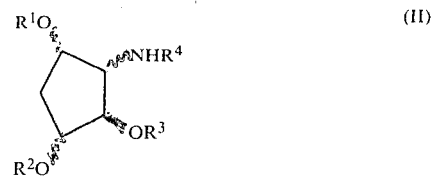

(II)

wherein R$^1$ to R$^4$ are defined above, with a compound of Formula III

R$^5$—X (III)

wherein X is Cl, Br, I an azido, an alkylsulphonyloxy or an arylsulphonyloxy group and R$^5$ is as defined above.

Alternatively a compound of Formula IV

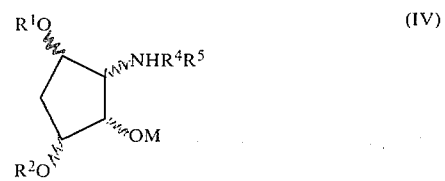

(IV)

wherein M is H or the equivalent moieties of an alkali metal or alkaline earth metal atom, R$^1$ and R$^2$ are benzyl and R$^4$ and R$^5$ are as defined above, can be reacted with a compound of Formula V

R$^3$—X (V)

wherein R$^3$ and X are as defined above.

Also, a compound of Formula VI

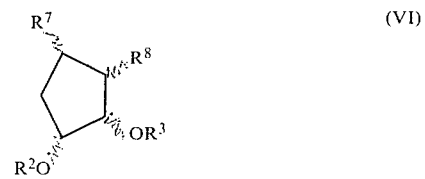

(VI)

wherein R$^7$ is OR$^1$ or, together with R$^8$, is an oxygen atom, and R$^8$ is X or, together with R$^7$, an oxygen atom and R$^1$, R$^2$, R$^3$ and X are as defined above, or one of Formula VII

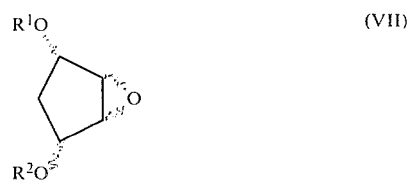

(VII)

wherein R$^1$ and R$^2$ are as defined above, can be reacted with a compound of Formula VIII

R$^4$R$^5$NH (VIII)

wherein R$^4$ and R$^5$ are as defined above.

Furthermore a compound of Formula IX

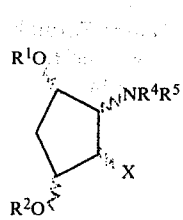
(IX)

wherein $R^1$, $R^2$, $R^4$, $R^5$ and X are as defined above can be reacted with a compound of Formula X $$R^3OM \qquad (X)$$

wherein $R^3$ and M are as defined above.

Moreover, a compound of Formula XI

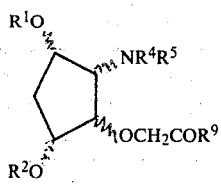
(XI)

wherein $R^1$, $R^2$, $R^4$ and $R^5$ are as defined above and $R^9$ is alkyl of 3-8 C-atoms, may be reacted with a hydrogenating agent.

Other preparative reactions include changing, in a compound of Formula XII

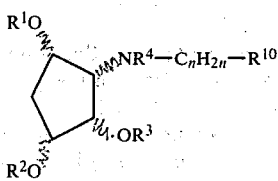
(XII)

wherein $R^{10}$ is a residue convertible into a $COOR^6$ group and $R^1$ to $R^4$ and n are as defined above, the residue $R^{10}$ into a $COOR^6$ group by reaction with a solvolysing agent; and/or converting a compound of Formula I wherein $R^1$ and/or $R^2$=benzyl, by reaction with a hydrogenolysing or hydrolysing agent, into another compound of Formula I having $R^1$ and $R^2$=H; and/or converting a compound of Formula I wherein $R^6$=H, by reaction with an esterifying agent, into another compound of Formula I having $R^6$=alkyl of 1 to 4 C-atoms; and/or converting a compound of Formula I wherein $R^6$=alkyl of 1 to 4 C-atoms, by reaction with a solvolysing agent, into another compound of Formula I having $R^6$=H or alkyl of 1 to 4 C-atoms; and/or converting a compound of Formula I wherein $R^4$=H, by reaction with a methylating or an ethylating agent into another compound of Formula I having $R^4$=methyl or ethyl; and/or separating a compound of Formula I into its racemates and/or optical antipodes; and/or converting a compound of Formula I, by reaction with an acid or a base, into one of its physiologically acceptable salts; and/or liberating a compound of Formula I from one of its salts by reaction with a base or an acid.

The compounds of Formula II are partially new and partially known. $R^1$ to $R^4$ are as defined for Formula I, especially those mentioned as being preferred. The new compounds of Formula II can be prepared according to standard methods known from the literature, for example, according to the following reaction sequence:

An epoxide of Formula VII is reacted with an amine $R^4NH_2$ to give the aminoalcohol of Formula XIII

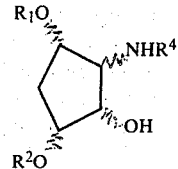
(XIII)

wherein $R^1$, $R^2$ and $R^4$ are as defined above. This, in turn, is reacted with e.g. tert-butyloxycarbonyl azide (III; $R^5$=—$C_nH_{2n}$COO-tert-$C_4H_9$, n=0, X=$N_3$) to give a compound of Formula XIV

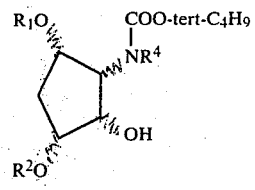
(XIV)

The compound of Formula XIV is now, in turn, reacted with a compound of formula V (X=I) in the presence of a base or freshly precipitated silver oxide to give a compound In

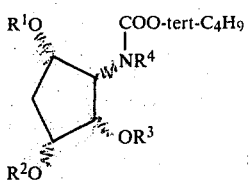
(In)

from which the desired compound of Formula II is obtained, e.g. by treatment with trifluoroacetic acid.

The compounds of the Formula III are known. $R^5$ is as defined above for Formula I, especially those said to be preferred. X preferably is Br or I but also Cl, alkylsulphonyloxy of preferably up to 4 C-atoms, such as methylsulphonyloxy or ethylsulphonyloxy, or arylsulphonyloxy of preferably up to 10 C-atoms, such as phenylsulphonyloxy, p-tolylsulphonyloxy or α-naphthylsulphonyloxy, and, when $R^5$ is —COO-tert-$C_4H_9$, especially also an $N_3$ group.

The reaction of a compound of Formula II with a compound of Formula III can be performed either by reaction of the pure components with one another or preferably also in the presence of solvents, e.g. hydrocarbons, such as benzene, toluene, xylene; halogenated hydrocarbons, such as chloroform, 1,2-dichloroethane, chlorobenzene; ketones, such as acetone or butanone; aprotic dipolar solvents, such as dimethyl formamide (+DMF), acetonitrile, dimethyl sulphoxide, tetramethylurea, tetrahydrothiophene-1,1-dioxide; alcohols, such as methanol, ethanol; ethers, such as tetrahydrofuran or dioxane; and optionally also in mixtures of these solvents with one another or with water. The addition of an acid-binding agent is favorable, for example, a hydroxide, carbonate, bicarbonate or another salt of a weak acid of the alkali or alkaline earth metals, preferably of sodium, potassium or calcium; or an organic base, such as triethylamine, dimethylaniline, pyridine or quinoline. Depending upon the reaction conditions, the reaction time lies between about a few minutes and 24 hours; and the reaction temperature between about 20° and 180° C., preferably at the boiling point of the reaction mixture.

The compounds of Formula IV are partially new and partially known. $R^1$ and $R^2$ are benzyl. $R^4$ and $R^5$ are as defined for Formula I, especially those stated to be preferred. Besides H, M can be the equivalent moities, an alkali or alkaline earth metal atom, preferably sodium or potassium.

The compounds of the Formula IV can, in turn, be obtained, for example, by reaction of a compound of the formula VII wherein $R^1=R^2=$benzyl with a compound of Formula VIII and optional conversion of the di-benzyloxyaminocyclopentanol obtained into the corresponding alkali or alkaline earth metal alcoholate, for example using alkali metal or alkaline earth metal hydrides, such as NaH.

The compounds of Formula V are known. $R^3$ is as defined above for Formula I, especially those stated to be preferred. The reaction of compounds IV and V is performed under conditions known for the conventional reaction and described in detail in the literature. The reaction partners can be reacted with one another in stoichiometric amounts. However, it is more expedient to use the etherification agent of Formula V in excess. It is especially advantageous to prepare the compounds of the Formula IV wherein M is different from H, in situ, i.e., from the compounds of Formula IV, in which M is hydrogen. The free alcohols of Formula IV can also be reacted with the compounds of Formula V in the presence of catalysts, such as sodium or potassium hydroxide or sodium or potassium carbonate, or also in the presence of catalytic amounts of a tertiary amine, such as pyridine, collidine or triethylamine, which can also serve as solvent, but especially in the presence of silver oxide. Preferably, the reaction is conducted in the presence of a solvent, for example a hydrocarbon, such as benzene, toluene or xylene, or, especially in the case of the presence of potassium carbonate as basic catalyst, using ketones, such as acetone, as solvent. Especially suitable solvents also include aprotic-dipolar solvents, such as DMF, dimethyl sulphoxide or dimethyl acetamide. The reaction temperatures for the etherification preferably lie between about 40° and about 140° C., especially at the boiling point of the reaction mixture. The reaction times are essentially dependent upon the nature of the etherification agent of the Formula V and upon the chosen reaction temperature; in general, they lie between about 30 minutes and about 24 hours.

The compounds of the Formula VI are partially known, and partially new. $R^2$ is preferably benzyl and $R^3$ is as defined for Formula I, especially those stated to be preferred. $R^7$ is preferably either benzyloxy or, together with $R^8$, an oxygen atom. $R^8$ is either X, as defined for Formula III, or, together with $R^7$, an oxygen atom. The compounds of Formula VI wherein $R^7=$benzyloxy and $R^8=$X are obtainable, for example, by reaction of a compound of Formula VII wherein $R^1=R^2=$benzyl with a sodium alcoholate NaOR$^3$; hydrolytic working-up of the reaction product; and reaction of the 2-R$^3$O-3,5-dibenzyloxy-cyclopentanol obtained for example with hydrochloric acid in the presence of zinc chloride, to give the desired starting compound of Formula VI ($R^8=$Cl).

When in the compounds of Formula VI, $R^7$ together with $R^8$ is an oxygen atom, the resultant epoxy compounds have the Formula VIa

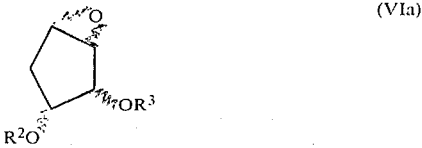

wherein $R^2$ and $R^3$ are as defined above for Formula I, especially those stated to be preferred.

The compounds of Formula VIa are obtainable, for example, by reaction of the known 3-cyclopenten-1-ol with sodium hydride to give the corresponding sodium alcoholate; conversion of the sodium alcoholate with benzyl chloride into the 3-benzyloxy-cyclopentene; bromination in the allyl position, for example with N-bromosuccinimide; reaction of the 2-bromo-3-benzyloxy-cyclopentene obtained with a sodium alcoholate of the Formula X and epoxidation of the product obtained, for example with m-chloroperbenzoic acid.

The most important compound of the Formula VII is the known 1,4-dibenzyloxy-2,3-epoxy-cyclopentane. The other two compounds of Formula VII are also known or conventionally preparable. The compounds of Formula VIII, are in the greater part known. The new compounds of Formula VIII can be prepared in analogy to the known compounds of the Formula VIII, for example, by reaction of an amine $R^4NH_2$ with a compound of Formula III.

In a compound of Formula VIII, the radicals $R^4$ and $R^5$ are as defined above for Formula I, especially those stated to be preferred.

The reaction of a compound of Formula VI or VII with a compound of Formula VIII, is a conventional nitrogen alkylation. Therefore, it can be conducted under the reaction conditions known for such reactions and described in great detail in the literature. Preferably the reaction parameters discussed above for the reaction of a compound of Formula II with a compound of the Formula III are employed. This is also true when the compounds of Formula VI are the epoxides of Formula VIa.

The compounds of Formula IX are partially new and partially known. The radicals $R^1$, $R^2$, $R^4$, $R^5$ and X are as defined above for Formula I or III, especially those stated to be preferred. It is especially advantageous to use as starting products those compounds of Formula IX in which $R^1=R^2=$benzyl. The compounds of Formula IX are obtainable, for example, from 2-cyclopenten-1,4-diol by conversion into the corresponding disodium alcoholate (for example with NaH); reaction with benzyl chloride; addition or bromine to the 3,5-dibenzyloxy-cyclopentene obtained and reaction of the so-obtained 1,4-dibenzyloxy-2,3-dibromo-cyclopentane with an equivalent amount of a compound of Formula VIII. In this way, there are obtainable, for example, the compounds of Formula IX with X=Br.

The compounds of Formula X are known.

The reaction of a compound of Formula IX with a compound of Formula X is an oxygen, alkylation, more precisely an oxygen cycloalkylation. Therefore, the reaction conditions known for such reactions and described more exactly in the literature can be used. Preferably those reaction conditions mentioned above for the reaction of a compound of Formula IV with a compound of Formula V can be used. In an especially advantageous variant, the compounds of Formula X wherein M is different from H are prepared in situ from the alcohols of Formula X (M=H) upon which they are based. Advantageously, a basic catalyst is then used, for example an alkali or alkaline earth metal hydroxide or an alkali or alkaline earth metal carbonate, especially potassium carbonate. In this variant, expediently, DMF is used as solvent.

Compounds of Formula XI can be converted with hydrogenating agents, preferably complex metal hydrides, such as sodium borohydride or lithium aluminium hydride, into the desired compounds of Formula I wherein $R^3$=2-hydroxyalkyl of 5-10 C-atoms. The reduction can also be effected using aluminium alkoxides according to the method of Meerwein-Ponndorf. The reaction conditions for such reductions are known (cf., e.g., L. F. Fieser, M. Fieser, *Reagents for Organic Synthesis*, John Wiley & Sons, Inc., New York—London—Sydney, 1967, page 35).

Most of the compounds of Formula XI are new. They can be prepared, for example, from the compounds of Formula IV, wherein $R^1=R^2$=benzyl and $R^4$ is other than hydrogen, by reaction with bromomethyl ketones $CH_2BrCOR^9$. In some cases, the use of such bromomethyl ketones is advantageous, since these compounds are more reactive than the corresponding carbinols $CH_2BrCH(OH)R^9$.

In formula XI, $R^9$ is an alkyl radical of 3-8 C-atoms. Preferred radicals $R^9$ are unbranched alkyl radicals of 3-8 C-atoms, such as propyl, butyl, hexyl, heptyl, octyl or especially pentyl.

The compunds of the Formula XII are also preponderantly new. They can be obtained in simple manner from the compounds of Formula II by reaction with compounds of Formula XV

$$X-C_nH_{2n}R^{10} \qquad (XV)$$

wherein n is as defined for Formula I, X is an defined for Formula III and $R^{10}$ is as defined for Formula XII.

$R^{10}$ is a residue convertible into a $COOR^6$ group. Suitable such groups, in principle, include solvolysable residues, preferably a functionally changed carboxyl group, especially a nitrogen-containing functionally changed carboxyl group, such as $-CON_3$, $-CONR^{11}R^{12}$, $-C(=NH)OR^{15}$ or $-C\equiv N$; or a functionally changed carboxyl group containing only oxygen, especially $-C(OR^{11})_3$. $R^{11}$ and $R^{12}$ may be the same or different and each is in addition to H, an organic radical, for example, an alkyl group, preferably unbranched, and especially of up to 4 C-atoms; alkyl of up to 4 C-atoms substituted by Cl, Br, I, OH, alkoxy of up to 4 C-atoms, acyloxy of up to 4 C-atoms, phenyl or naphthyl; cycloalkyl of up to 6 C-atoms; aryl of up to 10 C-atoms optionally substituted one or more times by Cl, Br, $NO_2$, OH, alkoxy of up to 4 C-atoms, acyloxy of up to 4 C-atoms or combinations thereof; and organo-silicon radicals, preferably trialkylsilyl, for example trimethylsilyl. Together $R^{11}$ and $R^{12}$ can also be polymethylene of up to 6 C-atoms, such as $-(CH_2)_4-$, $-(CH_2)_5-$ or $-(CH_2)_6-$; or polymethylene of preferably up to 6 C-atoms interrupted by O, N or S atoms.

Compounds of Formula XII, in which the radical $R^{10}$ is a functionally changed carbonyl group, can be solvolysed or thermolysed, especially hydrolysed, according to methods described in the literature, to give the compounds of Formula I. The hydrolysis may be carried out in acidic or also alkaline medium at temperatures between $-20°$ and $300°$ C., preferably at the boiling temperature of the chosen solvent. Suitable acid catalysts include, for example, hydrochloric, sulphuric, phosphoric or hydrobromic acid; basic catalysts expediently include sodium, potassium or calcium hydroxide, or sodium or potassium carbonate. Suitable solvents include alcohols, such as ethanol and methanol; ethers, such as dioxane and tetrahydrofuran; or mixtures thereof, especially with water.

In particular, the compounds of Formula I can also be obtained by solvolysis of nitriles of the Formula XII ($R^{10}$=CN). This solvolysis can be carried out as an hydrolysis in a per se known fashion in aqueous media producing the acids of Formula I, or it can be carried out analogously to the methods described in the literature with the exclusion of water and in the presence of an alcohol then producing the esters of Formula I. The reaction is carried out in the presence of an acidic or basic catalyst.

If a basic catalyst is used, preferably an alkali metal or alkaline earth metal hydroxide is used, such as NaOH, KOH or $Ba(OH)_2$, or also a basic salt, such as $K_2CO_3$ or $Na_2CO_3$. $H_2O$ or $H_2O$/alcohol mixtures are employed at elevated temperature, preferably at the boiling point of the reaction mixture, optionally also in an autoclave at elevated pressure.

The solvolysis of amides of Formula XII ($R^{10}$=$CONR^{11}R^{12}$) takes place under the reaction conditions described above for nitriles.

The compounds of Formula I wherein $R^1=R^2$=H are obtained from other compounds of Formula I having $R^1$ and/or $R^2$=benzyl by treatment with a hydrogenolysing or a hydrolysing agent. Hydrogenolysing agents include either chemically or catalytically activated hydrogen. Hydrogenolysis with hydrogen in the presence of a Pd catalyst, e.g. Pd charcoal is preferred. The hydrogenolysis is expediently carried out in a suitable solvent, for example in an alcohol, such as methanol or ethanol; a carboxylic acid, such as acetic acid; or an ester, such as ethyl acetate. The reaction takes place between $-20°$ and $+140°$ C., preferably between $+10°$ and $+40°$ C.

However, it is also possible to hydrogenolyse, e.g., with lithium in liquid ammonia. Hydrolyses takes place, e.g., with water in the presence of strong acids, such as $H_2SO_4$, but also with Lewis acids, such as $BF_3$ (as etherate).

Compounds of Formula I wherein $R^6$=H can be esterified according to per se known methods with an esterifying agent. Suitable esterifying agents include, for example, alcohols of up to 4 C-atoms, preferably in the presence of an inorganic or organic acid such as HCl, HBr, HI, $H_2SO_4$, $H_3PO_4$ or trifluoroacetic acid, of a sulphonic acid, such as benzenesulphonic acid or p-toluenesulphonic acid, or of an acidic ion exchanger; diazoalkanes of up to 4 C-atoms, preferably diazomethane; olefins (e.g. isobutylene), preferably in the presence of acidic catalysts (e.g. $ZnCl_2$, $BF_3$, $H_2SO_4$, arylsulphonic acid, pyrophosphoric acid, boric acid or oxalic acid); alkyl halides of up to 4 C-atoms, preferably bromides, such as ethyl, propyl, isopropyl or butyl bromide, and also the corresponding chloride or iodides; carboxylic acid or sulphonic acid alkyl esters, whereby the acid residue can be as desired and the alkyl radical contains up to 4 C-atoms, preferably methyl, ethyl, propyl, isopropyl or butyl acetate, formate, methylsulphonate, ethylsulphonate or p-toluenesulphonate; and especially also the alkyl sulphuric acid esters of up to 4 C-atoms, such as dimethyl sulphate or diethyl sulphate.

The esterification occurs in a suitable inert, preferably anhydrous solvent, for example, an ether, such as diethyl ether or THF; an alkanol, such as methanol, ethanol, propanol, isopropyl alcohol or butanol; hydrocarbon, such as petroleum ether, hexane, benzene or toluene; or mixtures of these solvents, at temperatures between about $-10°$ and $85°$ C. As a rule, the reaction times lie between 30 minutes and 24 hours. It is especially advantageous to carry out an esterification using diazoalkanes, especially with diazomethane or diazoethane.

The saponification of compounds of Formula I wherein $R^6$=alkyl of 1-4 C-atoms to other compounds of the formula I having $R^6$=H takes place according to per se known methods by reaction with aqueous bases, e.g. aqueous solutions of alkali metal hydroxides or carbonates, such as NaOH, KOH or $Na_2CO_3$.

The compounds of Formula I wherein $R^6$=alkyl of 1-4 C-atoms, can also be converted by reaction with a solvolysing agent, into another compound of Formula I having $R^6$=alkyl of 1-4 C-atoms. This reaction is a transesterification, whereby, as solvolysing agent, there can be used, for example, the above-mentioned carboxylic acid alkyl esters in which the carboxylic acid residue can be as desired and the alkyl radical originating from the alcoholic component of the ester contains up to 4 C-atoms.

One of the obtained compounds of the Formula I wherein $R^4$=H, can also be converted by reaction with a methylating or ethylating agent, into another compound of Formula I having $R^4$=methyl or ethyl. Suitable methylating or ethylating agents, include the compounds $CH_3X$ or $C_2H_5X$, in which X is as defined above for Formula III. Preferred methylating or ethylating agents include methyl bromide, methyl iodide, ethyl bromide or ethyl iodide. The methylation or ethylation can be carried out as the nitrogen alkylation under the reaction conditions given above e.g. for the reaction of a compound of formula II with a compound of Formula III.

As mentioned above, the compounds of Formula I have, in general, several centers of asymmetry but always at least four. Therefore, they are primarily obtained as mixtures of different stereoisomeric forms, i.e. as racemates or, as a rule, as mixtures of racemates. Since different racemates are diastereomeric to one another, they can, on the basis of their different physical properties, be isolated from their mixtures and obtained in pure form, for example by recrystallisation from suitable solvents (whereby, instead of the compounds themselves, there can also be used well crystallising derivatives); by distillative separation; but especially by chromatographic methods, including not only adsorption chromatographic or partition chromatographic methods but also mixed forms.

The racemates can be separated into their optical antipodes by a plurality of known methods, such as are given in the literature. The method of chemical separation is preferred. Thereby, diastereomers are formed from a racemic mixture by reaction with an optically-active adjuvant.

Thus, an optically-active base can be reacted with the carboxyl group of a compound of Formula I. For example, diastereomeric salts of the compounds of Formula I ($R^6$=H) can be formed with optically-active amines, such as quinine, brucine, 1-phenyl-ethylamine, 1-($\alpha$-naphthyl)-ethylamine, or basic amino acids, such as lysine or arginine. Similarly, ester diastereomers can be prepared by esterification of compounds of Formula I ($R^6$=H) with optically-active alcohols, such as borneol, menthol or octan-2-ol. The difference in the solubility of the diastereomeric salts or esters obtained permits the selective crystallisation of one form and the regeneration of the particular optically-active compounds from the mixture.

However, the amino group in these compounds of Formula I can also be reacted with an optically-active acid, such as (+)- and (−)-tartaric acid, dibenzoyl-(+)- and (−)-tartaric acid, camphoric acid, $\beta$-camphorsulphonic acid, (+)- and (−)-2-phenylbutyric acid or (+)- and (−)-dinitrodiphenic acid. Here, too, the racemate resolution is possible based on the different solubilities of the diastereomeric salts obtained.

Furthermore, it is naturally possible to obtain optically-active compounds according to the described methods by using starting materials which are themselves optically-active.

One can convert the free carboxylic acids of Formula I ($R^6$=H), by reaction with a base, into one of their physiologically acceptable metal or ammonium salts. Suitable salts include sodium, potassium, magnesium, calcium and ammonium salts, and substituted ammonium salts, such as, e.g., the dimethyl and diethyl ammonium, monoethanol, diethanol and triethanol ammonium, cyclohexyl ammonium, dicyclohexyl ammonium and dibenzyl ethylene diammonium salts. On the other hand, acids of Formula I can be liberated from their metal and ammonium salts by treatment with acids, especially mineral acids, such as hydrochloric or sulphuric acid. A base of Formula I can be converted with an acid into the related acid-addition salt. For this reaction, suitable acids are those which provide physiologically acceptable salts. Thus, inorganic acids can be used, e.g. sulphuric acid, nitric acid; hydrohalic acids, such as hydrochloric acid or hydrobromic acid; and phosphoric acids, such as orthophosphoric acid. Furthermore, organic acids, especially aliphatic, alicyclic, araliphatic, aromatic or heterocyclic mono- and polybasic carboxylic, sulphonic or sulphuric acids, can be used such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicycic acid, 2-phenyl-propionic acid, citric acid, gluconic acid, ascorbic acid, nicotinic acid, isonicotinic acid, methane- or ethane-sulphonic acid, ethane-disulphonic acid, 2-hydroxyethane-sulphonic acid, benzene-sulphonic acid, p-toluene-sulphonic acid, naphthalene-mono- and disulphonic acids or lauryl-sulphuric acid. On the other hand, the bases of Formula I can be liberated from their acid-addition salts by treatment with a base, especially an inorganic base, such a NaOH or KOH.

It has been found that the prostaglandin-like compounds of Formula I possess valuable pharmacological properties. Thus, in particular, they exhibit thrombocyte aggregation-inhibiting and/or adhesion-inhibiting properties which can be demonstrated, for example, in analogy to the method of Born, Nature (London), 194 (1962). Therefore, the compounds of Formula I can be used as medicaments and also as intermediate products for the preparation of other medicaments.

For such medicaments, the new compounds of Formula I can be mixed with at least one solid liquid and/or semi-liquid carrier or adjuvant material conventional in pharmacy. The mixtures of the compounds of Formula I with the carrier or adjuvant materials customary in pharmacy can be used as medicines in human or veterinary medicine. Suitable carrier materials include those organic or inorganic materials which are suitable for parenteral, enteral (e.g. oral) or topical administration and do not react with the new compounds of Formula I, for example, water, vegetable oils, benzyl alcohols, polyethylene, glycols, glycerol triacetate, gelatine, lactose, starch, magnesium stearate, talc, vaseline, cholesterol. For oral administration, there are suitable tablets, dragees, capsules, syrups, juices or drops; for rectal administration suppositories; for parentereal administration solutions, preferably oily or aqueous solutions, furthermore, suspensions, emulsions or implants; and for topical administration salves, creams or powders.

The new compounds can also be lyophilised and the lyophilisates obtained used e.g. for the production of injection preparations. The stated compositions can be sterilised and/or mixed with adjuvant materials, such as lubricating, preserving, stabilising or wetting agents, emulsifiers, salts for the influencing of the osmotic pressure, buffer substances, coloring, flavoring and/or aroma generating materials. If desired, they can also contain one or more additional active materials, e.g. one or more vitamins.

The compounds of this invention are, as a rule, administered in analogy to known, commercially available thrombosis prophylactics, preferably in dosages between about 1 and 500 mg, especially between 5 and 50 mg per dosage unit. The daily dosage normally lies between about 0.02 and 10 mg/kg of body weight. The particular dose for each particular patient depends, however, upon the most varied factors, for example, upon the effectiveness of the specific compound used, upon the age, body weight, general state of health, sex and diet of the patient, upon the time point and route of administration, upon the rate of excretion, upon the combination of medicines administered and upon the severity of the particular disease to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

IR spectra (IR) are characterised by statement of the main bands (as a film).

The NMR spectra (NMR) were measured in CDCl$_3$ against tetramethylsilane and are characterised by statement of the signals in ppm, wherein m=multiplet, q=quartet, t=triplet, d=doublet and s=singlet.

Each of the compounds of Formula I mentioned in the following Examples is especially suitable for the preparation of medicaments.

It is to be noted that the specification of the symbols $\alpha$ and $\beta$ does not signify the ascertainment of the absolute configuration but only the relative positions of the substituents. Whenever there is no indication of the $\alpha$- or $\beta$-position, the radical can assume both orientations.

EXAMPLE 1

20 g of 1$\alpha$,4$\alpha$-dibenzyloxy-2$\alpha$,3$\alpha$-epoxycyclopentane are heated for 20 hours with 400 ml of a 40% methylamine solution in methanol in an autoclave at 100° and, after distilling off the solvent, as residue, 3$\alpha$-5$\alpha$-dibenzoyloxy-2$\beta$-methylamino-1$\alpha$-cyclopentanol is obtained; m.p. 50°–52° (from petroleum ether).

EXAMPLE 2

16 g of 3$\alpha$,5$\alpha$-dibenzyloxy-2$\beta$-methylamino-1$\alpha$-cyclopentanol are mixed with 3.1 g of MgO. This mixture is suspended in 140 ml of 50% aqueous dioxane. Thereto, with stirring, 11 g of tert-butyloxycarbonyl azide are added dropwise. The mixture is stirred for 16 hours at 50° and allowed to stand overnight at ambient temperature. The lower phase is separated off and stirred into 500 ml of water. This is extracted 3 times with 100 ml amounts of ethyl acetate. The organic phase is washed twice with 60 ml amounts of aqueous NaHCO$_3$ solution and once with 60 ml of water. It is dried over sodium sulphate and the solvent distilled off. After chromatographic purification of the residue (silica gel/chloroform), 3$\alpha$,5$\alpha$-dibenzyloxy-2$\beta$(N-methyl-N-tert.-butoxycarbonylamino)-1$\alpha$-cyclopentanol is obtained;

IR: 700, 740, 1670 and 3450 cm$^{-1}$.

EXAMPLE 3

With stirring, to a mixture consisting of 4.3 g of 3$\alpha$,5$\alpha$-dibenzyloxy-2$\beta$-(N-methyl-N-tert.-butyloxycarbonylamino)-1$\alpha$-cyclopentanol, 20 ml of dry DMF and 6.9 g of silver oxide, at 80° within the course of 4 hours, 13.55 g of 1-iodoheptane, dissolved in 20 ml of dry DMF is dropped. The mixture is further stirred for 16 hours at 80°, and the solvent substantially distilled off. After chromatographic purification of the residue (silica gel/methylene chloride: acetone=9:1), N-methyl-N-tert.-butyloxycarbonyl-5$\alpha$-heptyloxy-2$\alpha$,4$\alpha$-dibenzyloxycyclopentane-1$\beta$-amine is obtained;

IR: 1700, 735 and 695 cm$^{-1}$,

NMR: 0.9 (t), 1.4 (s), 2.95 (s), 4.5 (s), 4.65 (s), 7.3 (s).

EXAMPLE 4

(a) A mixture consisting of 0.8 g of N-methyl-N-tert-butoxycarbonyl-5$\alpha$-heptyloxy-2$\alpha$,4$\alpha$-dibenzyloxy-cyclopentane-1$\beta$-amine and 1 ml of trifluoroacetic acid is allowed to stand for 24 hours at room temperature, is stirred into 5 ml of saturated aqueous sodium bicarbonate solution, and is extracted 3 times with 10 ml amounts of diethyl ether. The combined organic phases are washed with water and dried over sodium sulphate. Dry HBr gas is passed in and the hydrobromide of N-methyl-5$\alpha$-heptyloxy-2$\alpha$,4$\alpha$-dibenzyloxy-cyclopentane-1$\beta$-amine, m.p. 138° (from acetone/diethyl ether) is obtained.

(b) 0.5 g of the hydrobromide of N-methyl-5$\alpha$-heptyloxy-2$\alpha$,4$\alpha$-dibenzyloxy-cyclopentane-1$\beta$-amine is treated with aqueous 1 N aqueous sodium hydroxide solution. This is extracted with diethyl ether, and the ether phase is washed neutral with water. It is dried over sodium sulphate. After distilling off the solvent, N-methyl-5$\alpha$-heptyloxy-2$\alpha$,4$\alpha$-dibenzyloxy-cyclopentane-1$\beta$-amine is obtained;

IR: 700, 740 cm$^{-1}$,

NMR: 0.9 (t), 2.5 (s), 4.55 (m) and 7.3 (s).

EXAMPLE 5

For 18 hours a mixture consisting of 2.3 g of N-methyl-5$\alpha$-heptyloxy-2$\alpha$,4$\alpha$-dibenzyloxy-cyclopentane-1$\beta$-amine, 2.1 g of 1-iodoheptane and 40 ml of dry ethanol is boiled. The solvent is distilled off. After chromatographic purification of the residue (silica gel/- chloroform:acetone=9:1), N-heptyl-N-methyl-5α-heptyloxy-2α,4α-dibenzyloxy-cyclopentane-1β-amine is obtained.

NMR: 0.9 (t), 2.0 (t), 2.6 (s), 2.6 (m), 7.3 (s).

EXAMPLE 6

A mixture consisting of 1.4 g of N-heptyl-N-methyl-5α-heptyloxy-2α,4α-dibenzyloxy-cyclopentane-1β-amine, 37 ml of dry benzene and 14 ml of boron trifluoride etherate is allowed to stand for 6 days at room temperature. The reaction mixture is stirred into aqueous sodium bicarbonate solution (pH value about 7). The organic phase is separated and the aqueous phase extracted with chloroform. The organic phases are combined and dried over sodium sulphate. The solvent is distilled off. After chromatographic purification of the residue (silica gel/chloroform:methanol = 85:15), N-heptyl-N-methyl-5α-heptyloxy-2α,4α-dihydroxycyclopentane-1β-amine is obtained;

NMR: 0.9 (t), 2.45 (s),
IR: 3350 cm$^{-1}$.

EXAMPLES 7–23

Analogously to Example 5, by reaction of N-methyl-5α-heptyloxy-2α,4α-dibenzyloxy-cyclopentane-1β-amine with the corresponding compounds of Formula III (X=I), the following compounds of Formula I are obtainable:

Examples of Compounds of Formula I

7. N-pentyl-N-methyl-5α-heptyloxy-2α,4α-dibenzyloxy-cyclopentane-1β-amine,
8. N-hexyl-N-methyl-5α-heptyloxy-2α,4α-dibenzyloxy-cyclopentane-1β-amine,
9. N-octyl-N-methyl-5α-heptyloxy-2α,4α-dibenzyloxy-cyclopentane-1β-amine,
10. N-nonyl-N-methyl-5α-heptyloxy-2α,4α-dibenzyloxy-cyclopentane-1β-amine,
11. N-decyl-N-methyl-5α-heptyloxy-2α,4α-dibenzyloxy-cyclopentane-1β-amine,
12. N-(1-methylpentyl)-N-methyl-5α-heptyloxy-2α,4α-dibenzyloxy-cyclopentane-1β-amine,
13. N-(1-methylhexyl)-N-methyl-5α-heptyloxy-2α,4α-dibenzyloxy-cyclopentane-1β-amine,
14. N-(1-methylheptyl)-N-methyl-5α-heptyloxy-2α,4α-dibenzyloxy-cyclopentane-1β-amine,
15. N-(2-methylheptyl)-N-methyl-5α-heptyloxy-2α,4α-dibenzyloxy-cyclopentane-1α-amine,
16. N-(6,6-dimethylheptyl)-N-methyl-5α-heptyloxy-2α,4α-dibenzyloxy-cyclopentane-1β-amine,
17. N-(5-ethoxycarbonylpentyl)-N-methyl-5α-heptyloxy-2α,4α-dibenzyloxy-cyclopentane-1β-amine;
NMR: 0.85 (t), 1.25 (t), 3.75 (s), 4.1 (2d), 4.5 (m), 7.3 (s),
18. N-(5-methoxycarbonylpentyl)-N-methyl-5α-heptyloxy-2α,4α-dibenzyloxy-cyclopentane-1β-amine,
19. N-(4-ethoxycarbonylbutyl)-N-methyl-5α-heptyloxy-2α,4α-dibenzyloxy-cyclopentane-1β-amine,
20. N-(6-ethoxycarbonylhexyl)-N-methyl-5α-heptyloxy-2α,4α-dibenzyloxy-cyclopentane-1β-amine,
21. N-(5-methyl-5-ethoxycarbonylpentyl)-N-methyl-5α-heptyloxy-2α,4α-dibenzyloxy-cyclopentane-1β-amine,
22. N-(5-propyloxycarbonylpentyl)-N-methyl-5α-heptyloxy-2α,4α-dibenzyloxy-cyclopentane-1β-amine,
23. N-(5-butyloxycarbonylpentyl)-N-methyl-5α-heptyloxy-2α,4α-dibenzyloxy-cyclopentane-1β-amine.

EXAMPLES 24–36

Analogously to Example 3, from N-methyl-N-tert-butyloxycarbonyl-5α-hydroxy-2α,4α-dibenzyloxy-cyclopentane-1β-amine, by reaction with the corresponding compounds of Formula V, the following compounds of Formula I are obtainable:

Examples of Compounds of Formula I

24. N-methyl-N-tert-butyloxycarbonyl-5α-pentyloxy-2α,4α-dibenzyloxy-cyclopentane-1β-amine,
25. N-methyl-N-tert-butyloxycarbonyl-5α-hexyloxy-2α,4α-dibenzyloxy-cyclopentane-1β-amine,
26. N-methyl-N-tert-butyloxycarbonyl-5α-octyloxy-2α,4α-dibenzyloxy-cyclopentane-1β-amine,
27. N-methyl-N-tert-butyloxycarbonyl-5α-nonyloxy-2α,4α-dibenzyloxy-cyclopentane-1β-amine,
28. N-methyl-N-tert-butyloxycarbonyl-5α-(2-hydroxypentyloxy)-2α,4α-dibenzyloxy-cyclopentane-1β-amine,
29. N-methyl-N-tert-butyloxycarbonyl-5α-(2-hydroxyhexyloxy)-2α,4α-dibenzyloxy-cyclopentane-1β-amine,
30. N-methyl-N-tert-butyloxycarbonyl-5α-(2-hydroxyheptyloxy)-2α,4α-dibenzyloxy-cyclopentane-1β-amine,
31. N-methyl-N-tert-butyloxycarbonyl-5α-(2-hydroxy-2-methylheptyloxy)-2α,4α-dibenzyloxy-cyclopentane-1β-amine,
32. N-methyl-N-tert-butyloxycarbonyl-5α-(2-hydroxy-3,3-dimethylheptyloxy)-2α,4α-dibenzyloxy-cyclopentane-1β-amine,
33. N-methyl-N-tert-butyloxycarbonyl-5α-(2-hydroxy-2-3-dimethylheptyloxy)-2α,4α-dibenzyloxy-cyclopentane-1β-amine,
34. N-methyl-N-tert-butyloxycarbonyl-5α-(2-hydroxy-2,3,3-trimethylheptyloxy)-2α,4α-dibenzyloxy-cyclopentane-1β-amine,
35. N-methyl-N-tert-butyloxycarbonyl-5α-(2-hydroxyoctyloxy)-2α,4α-dibenzyloxy-cyclopentane-1β-amine,
36. N-methyl-N-tert-butyloxycarbonyl-5α-(2-hydroxynonyloxy)-2α,4α-dibenzyloxy-cyclopentane-1β-amine.

EXAMPLES 37–49

Analogously to Examples 4a and 4b, from the compounds of Formula I mentioned in Examples 24 to 35, by reaction with trifluoroacetic acid, precipitation of the reaction product as hydrobromide and treatment of the salt with NaOH, the following compounds of Formula II are obtainable:

Examples of Compounds of Formula I

37. N-methyl-5α-pentyloxy-2α,4α-dibenzyloxy-cyclopentane-1β-amine,
38. N-methyl-5α-hexyloxy-2α,4α-dibenzyloxy-cyclopentane-1β-amine,
39. N-methyl-5α-octyloxy-2α,4α-dibenzyloxy-cyclopentane-1β-amine,
40. N-methyl-5α-nonyloxy-2α,4α-dibenzyloxy-cyclopentane-1β-amine,
41. N-methyl-5α-(2-hydroxypentyloxy)-2α,4α-dibenzyloxy-cyclopentane-1β-amine,
42. N-methyl-5α-(2-hydroxyhexyloxy)-2α,4α-dibenzyloxy-cyclopentane-1β-amine,
43. N-methyl-5α-(2-hydroxyheptyloxy)-2α,4α-dibenzyloxy-cyclopentane-1β-amine, 44. N-methyl-5α-(2-hydroxy-2-methylheptyloxy)-2α,4α-dibenzyloxy-cyclopentane-1β-amine,
45. N-methyl-5α-(2-hydroxy-3,3-dimethylheptyloxy)-2α,4α-dibenzyloxy-cyclopentane-1β-amine,
46. N-methyl-5α-(2-hydroxy-2,3-dimethylheptyloxy)-2α,4α-dibenzyloxy-cyclopentane-1β-amine,
47. N-methyl-5α-(2-hydroxy-2,3,3-trimethylheptyloxy)-2α,4α-dibenzyloxy-cyclopentane-1β-amine,
48. N-methyl-5α-(2-hydroxyoctyloxy)-2α,4α-dibenzyloxy-cyclopentane-1β-amine,
49. N-methyl-5α-(2-hydroxynonyloxy)-2α,4α-dibenzyloxy-cyclopentane-1β-amine.

EXAMPLES 50–75

Analogously to Example 5, from the compounds of Formula II mentioned in Examples 37 to 49, by reaction with 1-iodoheptane or 6-iodohexanoic acid ethyl ester, the following compounds of Formula I are obtainable:

Examples of Compounds of Formula I

50. N-methyl-N-heptyl-5α-pentyloxy-2α,4α-dibenzyloxy-cyclopentane-1β-amine,
51. N-methyl-N-heptyl-5α-hexyloxy-2α,4α-dibenzyloxy-cyclopentane-1β-amine,
52. N-methyl-N-heptyl-5α-octyloxy-2α,4α-dibenzyloxy-cyclopentane-1β-amine,
53. N-methyl-N-heptyl-5α-nonyloxy-2α,4α-dibenzyloxy-cyclopentane-1β-amine,
54. N-methyl-N-heptyl-5α-(2-hydroxypentyloxy)-2α,4α-dibenzyloxy-cyclopentane-1β-amine,
55. N-methyl-N-heptyl-5α-(2-hydroxyhexyloxy)-2α,4α-dibenzyloxy-cyclopentane-1β-amine,
56. N-methyl-N-heptyl-5α-(2-hydroxyheptyloxy)-2α,4α-dibenzyloxy-cyclopentane-1β-amine,
57. N-methyl-N-heptyl-5α-(2-hydroxy-2-methylheptyloxy)-2α,4α-dibenzyloxy-cyclopentane-1β-amine,
58. N-methyl-N-heptyl-5α-(2-hydroxy-3,3-dimethylheptyloxy)-2α,4α-dibenzyloxy-cyclopentane-1β-amine,
59. N-methyl-N-heptyl-5α-(2-hydroxy-2,3-dimethylheptyloxy)-2α,4α-dibenzyloxy-cyclopentane-1β-amine,
60. N-methyl-N-heptyl-5α-(2-hydroxy-2,3,3-trimethylheptyloxy)-2α,4α-dibenzyloxy-cyclopentane-1β-amine,
61. N-methyl-N-heptyl-5α-(2-hydroxyoctyloxy)-2α,4α-dibenzyloxy-cyclopentane-1β-amine,
62. N-methyl-N-heptyl-5α-(2-hydroxynonyloxy)-2α,4α-dibenzyloxy-cyclopentane-1β-amine,
63. N-methyl-N-(5-ethoxycarbonylpentyl)-5α-pentyloxy-2α,4α-dibenzyloxy-cyclopentane-1β-amine,
64. N-methyl-N-(5-ethoxycarbonylpentyl)-5α-hexyloxy-2α,4α-dibenzyloxy-cyclopentane-1β-amine,
65. N-methyl-N-(5-ethoxycarbonylpentyl)-5α-octyloxy-2α,4α-dibenzyloxy-cyclopentane-1β-amine,
66. N-methyl-N-(5-ethoxycarbonylpentyl)-5α-nonyloxy-2α,4α-dibenzyloxy-cyclopentane-1β-amine,
67. N-methyl-N-(5-ethoxycarbonylpentyl)-5α-(2-hydroxypentyloxy)-2α,4α-dibenzyloxy-cyclopentane-1β-amine,
68. N-methyl-N-(5-ethoxycarbonylpentyl)-5α-(2-hydroxyhexyloxy)-2α,4α-dibenzyloxy-cyclopentane-1β-amine,
69. N-methyl-N-(5-ethoxycarbonylpentyl)-5α-(2-hydroxyheptyloxy)-2α,4α-dibenzyloxy-cyclopentane-1β-amine, NMR: 0.9 (t), 1.2 (t), 2.9 (s), 4.15 (m), 4.6 (m), 7.3 (s);
70. N-methyl-N-(5-ethoxycarbonylpentyl)-5α-(2-hydroxy-2-methylheptyloxy)-2α,4α-dibenzyloxy-cyclopentane-1β-amine,
71. N-methyl-N-(5-ethoxycarbonylpentyl)-5α-(2-hydroxy-3,3-dimethylheptyloxy)-2α,4α-dibenzyloxy-cyclopentane-1β-amine,
72. N-methyl-N-(5-ethoxycarbonylpentyl)-5α-(2-hydroxy-2,3-dimethylheptyloxy)-2α,4α-dibenzyloxy-cyclopentane-1β-amine,
73. N-methyl-N-(5-ethoxycarbonylpentyl)-5α-(2-hydroxy-2,3,3-trimethylheptyloxy)-2α,4α-dibenzyloxy-cyclopentane-1β-amine,
74. N-methyl-N-(5-ethoxycarbonylpentyl)-5α-(2-hydroxyoctyloxy)-2α,4α-dibenzyloxy-cyclopentane-1β-amine,
75. N-methyl-N-(5-ethoxycarbonylpentyl)-5α-(2-hydroxynonyloxy)-2α,4α-dibenzyloxy-cyclopentane-1β-amine.

EXAMPLES 76–97

Analogously to Example 6, from the dibenzyloxy compounds of Formula I mentioned in Examples 7 to 16 and 50 to 62, there are obtained, by reaction with boron trifluoride etherate, the following dihydroxy compounds.

Examples of Compounds of Formula I

76. N-pentyl-N-methyl-5α-heptyloxy-2α,4α-dihydroxy-cyclopentane-1β-amine,
77. N-hexyl-N-methyl-5α-heptyloxy-2α,4α-dihydroxy-cyclopentane-1β-amine,
78. N-octyl-N-methyl-5α-heptyloxy-2α,4α-dihydroxy-cyclopentane-1β-amine,
79. N-nonyl-N-methyl-5α-heptyloxy-2α,4α-dihydroxy-cyclopentane-1β-amine,
80. N-decyl-N-methyl-5α-heptyloxy-2α,4α-dihydroxy-cyclopentane-1β-amine,
81. N-(1-methylpentyl)-N-methyl-5α-heptyloxy-2α,4α-dihydroxy-cyclopentane-1β-amine,
82. N-(1-methylhexyl)-N-methyl-5α-heptyloxy-2α,4α-dihydroxy-cyclopentane-1β-amine,
83. N-(1-methylheptyl)-N-methyl-5α-heptyloxy-2α,4α-dihydroxy-cyclopentane-1β-amine,
84. N-(6,6-dimethylheptyl)-N-methyl-5α-heptyloxy-2α,4α-dihydroxy-cyclopentane-1β-amine,
85. N-methyl-N-heptyl-5α-pentyloxy-2α,4α-dihydroxy-cyclopentane-1β-amine,
86. N-methyl-N-heptyl-5α-hexyloxy-2α,4α-dihydroxy-cyclopentane-1β-amine,
87. N-methyl-N-heptyl-5α-octyloxy-2α,4α-dihydroxy-cyclopentane-1β-amine,
88. N-methyl-N-heptyl-5α-nonyloxy-2α,4α-dihydroxy-cyclopentane-1β-amine,
89. N-methyl-N-heptyl-5α-(2-hydroxypentyloxy)-2α,4α-dihydroxy-cyclopentane-1β-amine,
90. N-methyl-N-heptyl-5α-(2-hydroxyhexyloxy)-2α,4α-dihydroxy-cyclopentane-1β-amine,
91. N-methyl-N-heptyl-5α-(2-hydroxyheptyloxy)-2α,4α-dihydroxy-cyclopentane-1β-amine,
92. N-methyl-N-heptyl-5α-(2-hydroxy-2-methylheptyloxy)-2α,4α-dihydroxy-cyclopentane-1β-amine,
93. N-methyl-N-heptyl-5α-(2-hydroxy-3,3-dimethylheptyloxy)-2α,4α-dihydroxy-cyclopentane-1β-amine, 94. N-methyl-N-heptyl-5α-(2-hydroxy-2,3-dimethylheptyloxy)-2α,4α-dihydroxy-cyclopentane-1β-amine,
95. N-methyl-N-heptyl-5α-(2-hydroxy-2,3,3-trimethylheptyloxy)-2α,4α-dihydroxy-cyclopentane-1β-amine,
96. N-methyl-N-heptyl-5α-(2-hydroxyoctyloxy)-2α,4α-dihydroxy-cyclopentane-1β-amine,
97. N-methyl-N-heptyl-5α-(2-hydroxynonyloxy)-2α,4α-dihydroxy-cyclopentane-1β-amine.

EXAMPLE 98

A mixture of 0.5 g of N-(5-ethoxycarbonylpentyl)-N-methyl-5α-heptyloxy-2α,4α-dibenzyloxy-cyclopentane-1β-amine, 15 ml of methanol and 4.5 ml of aqueous 1 N sodium hydroxide solution is boiled for 2 hours. The reaction mixture is stirred in 50 ml of water and the pH is brought to a value of 6 with hydrochloric acid. The aqueous solution is extracted with chloroform; the organic phase is washed with water and dried over sodium sulphate; the solvent is distilled off; and after chromatographic purification of the residue (silica gel/chloroform:methanol=8:2), N-(5-hydroxycarbonylpentyl)-N-methyl-5α-heptyloxy-2α,4α-dibenzyloxy-cyclopentane-1β,amine is obtained.

IR: 1700, 740 and 700 cm$^{-1}$,
NMR: 0.8 (t), 2.5 (s), 4.5 (m), 7.3 (s).

The corresponding free acids of Formula I ($R^5 = -C_nH_{2n}COOH$) can be prepared analogously by saponification with methanolic sodium hydroxide solution from the esters of Formula I ($R^5 = -C_nH_{2n}COOR^6$, $R^6$ = other than hydrogen) mentioned in Examples 17 to 23 and 63 to 75.

EXAMPLE 99

Overnight, at room temperature, a mixture of 0.1 g of N-(5-ethoxycarbonylpentyl)-N-methyl-5α-heptyloxy-2α,4α-dibenzyloxy-cyclopentane-1β-amine, 2.5 ml of dry benzene and 1 ml of boron trifluoride etherate is stirred. Added thereto is an additional 1 ml of boron trifluoride etherate. Stirring is conducted for an additional 24 hours at 30°. The reaction mixture is stirred into a saturated aqueous sodium bicarbonate solution (pH = 4); the aqueous solution is extracted with chloroform; and the organic phase is washed with water, and dried over sodium sulphate. The solvent is distilled off and after chromatographic purification of the residue (silca gel/chloroform:methanol=8:2), N-(5-ethoxycarbonylpentyl)-N-methyl-5α-heptyloxy-2α,4α-dihydroxy-cyclopentane-1β-amine is obtained.

IR: 1730 and 3400 cm$^{-1}$,
NMR: 0.8 (t), 2.6 (s), 4.15 (2d).

The corresponding dihydroxy compounds of Formula I ($R^5 = -C_nH_{2n}COOR^6$, $R^6$ = other than hydrogen, $R^1 = R^2$ = hydrogen) are obtainable analogously from the dibenzyloxy compounds of Formula I ($R^5 = -C_nH_{2n}COOR^6$, $R^6$ = other than hydrogen, $R^1 = R^2$ = benzyl) mentioned in Examples 18 to 23 and 63 to 75.

EXAMPLE 100

Analogously to Example 99, from 1.4 g of N-(5-hydroxycarbonylpentyl)-N-methyl-5α-heptyloxy-2α,4α-dibenzyloxy-cyclopentane-1β-amine, by reaction with boron trifluoride ethereate, N-(5-hydroxycarbonylpentyl)-N-methyl-5α-heptyloxy-2α,4α-dihydroxy-cyclopentane-1β-amine is obtained;

IR: 1720 and 3350 cm$^{-1}$,
NMR: 0.95 (t) and 2.6 (s).

EXAMPLE 101

2.96 g. of 1α-4α-dibenzyloxy-2α,3α-epoxy-cyclopentane and 1.3 g of heptyl-methylamine are boiled for 12 hours in 40 ml of isopropyl alcohol. After cooling, this is poured into 60 ml of saturated aqueous NaCl solution. 5 ml of 1% aqueous NaOH solution is then added thereto. This is extracted with diethyl ether and the organic phase is dried over MgSO$_4$. The solvent is distilled off, after chromatographic purification (silica gel/chloroform), 3α,5α-dibenzyloxy-2β-(N-heptyl-N-methylamino)-1α-cyclopentanol is obtained.

EXAMPLES 102–110

Analogously to Example 101, the following compounds of Formula IV ($R^1 = R^2$ = benzyl, M = hydrogen) are obtainable by reaction of 1α,4α-dibenzyloxy-2α-3α-epoxycyclopentane with the corresponding amine of Formula VIII:

Examples of Compounds of Formula IV 102. 3α,5α-dibenzyloxy-2β-(N-heptyl-N-ethylamino)-1α-cyclopentanol,
103. 3α,5α-dibenzyloxy-2β-heptylamino-1α-cyclopentanol,
104. 3α,5α-dibenzyloxy-2β-(N-pentyl-N-methylamino)-1α-cyclopentanol,
105. 3α,5α-dibenzyloxy-2β-hexylamino-1α-cyclopentanol,
106. 3α,5α-dibenzyloxy-2β-(N-hexyl-N-methylamino)-1α-cyclopentanol,
107. 3α,5α-dibenzyloxy-2β-(N-hexyl-N-ethylamino)-1α-cyclopentanol,
108. 3α,5α-dibenzyloxy-2β-(N-octyl-N-methylamino)-1α-cyclopentanol,
109. 3α,5α-dibenzyloxy-2β-(N-nonyl-N-methylamino)-1α-cyclopentanol,
110. 3α,5α-dibenzyloxy-2β-(N-decyl-N-methylamino)-1α-cyclopentanol.

EXAMPLE 111

2.1 g of 3α-5α-dibenzyloxy-2β-(N-heptyl-N-methylamino)-1α-cyclopentanol, 0.9 g of heptyl bromide and 1.5 g of K$_2$CO$_3$ are stirred for 24 hours under N$_2$ at 60° in 30 ml of DMF. This is poured into 80 ml of saturated aqueous NaCl solution and extracted with benzene. The organic phase is dried over Na$_2$SO$_4$ and the solvent is distilled off. After chromatographic purification of the residue (silica gel/chloroform:acetone=9:1), N-heptyl-N-methyl-5α-heptyloxy-2α,4α-dibenzyloxy-cyclopentane-1β-amine is obtained;

NMR: 0.9 (t), 2.0 (t), 2.6 (s), 4.6 (m), 7.3 (s).

EXAMPLE 112

At 40°, under nitrogen and with stirring, within the course of 30 minutes, 5.25 g of 3α-5α-dibenzyloxy-2β-(N-heptyl-N-methylamino)-1α-cyclopentanol, dissolved in 80 ml of benzene is dropped into a suspension of 0.23 g of sodium in 70 ml of toluene. Stirring is conducted for 30 minutes at room temperature. 1.36 g of heptyl chloride, dissolved in 20 ml of benzene are dropped in and the solution stirred for 1 hour at 80°. After cooling, the precipitated sodium chloride is filtered off. The solvent is distilled off and after chromatographic purification of the residue (silica gel/chloroform:acetone=9:1), N-heptyl-N-methyl-5α-heptyloxy-2α,4α-dibenzyloxy-cyclopentane-1β-amine is obtained;
NMR: 0.9 (t), 2.0 (t), 2.6 (s), 4.6 (m), 7.3 (s).

EXAMPLE 113

3.04 g of 1,3-epoxy-4-benzyl-3-heptyl-oxycyclopentane and 1.3 g of heptyl-methylamine are boiled for 8 hours in 60 ml of isopropyl alcohol. The reaction mixture is worked up as described in Example 101 and after chromatographic purification (silica gel/chloroform), 4-benzyloxy-2-(N-heptyl-N-methylamino)-3-heptyloxy-1-cyclopentanol is obtained.

The starting material is obtainable as follows:

4-Benzyloxy-1-cyclopentene is brominated with N-bromosuccinimide in the 3-position. The 4-benzyloxy-3-bromo-1-cyclopentene obtained is reacted with 1-heptanol in the presence of silver oxide and the so obtained 4-benzyloxy-3-heptyloxy-1-cyclopentene is epoxidized with m-chloro-perbenzoic acid.

EXAMPLE 114

At 85° into a mixture of 1.3 g of heptyl-methylamine, 1.2 g of $K_2CO_3$ and 80 ml of dimethyl sulphoxide, within the course of 2 hours there is dropped 3.85 g of 4-benzyloxy-2-bromo-3-heptyloxy-1-cyclopentanol (obtainable from 1,2-epoxy-4-benzyloxy-3-heptyloxy-cyclopentane by reaction with HBr), dissolved in 40 ml of dimethyl sulphoxide. Further stirring occurs for 4 hours at 80°. After cooling, the mixture is poured into 250 ml of saturated aqueous NaCl solution, and this is exhaustively extracted with methylene chloride. The organic phase is dried with $Na_2SO_4$ and the solvent is distilled off. After chromatographic purification of the residue, 4-benzyloxy-3-heptyloxy-2-(N-heptyl-N-methylamino)-1-cyclopentanol. is obtained.

EXAMPLE 115

0.23 g of sodium are dissolved in 30 ml of 1-heptanol at 50° under nitrogen. Dropwise, with stirring, there is added 4.88 g of N-heptyl-N-methyl-2-bromo-4,5-bibenzyloxycyclopentane-1-amine (obtainable from 3,5-dibenzyloxy-2-cyclopentene by the addition of bromine and reaction with 1-equivalent of methyl heptylamine), dissolved in 30 ml of benzene. Stirring is carried on for 6 hours at 50°. After cooling, 100 ml of benzene is added thereto. This is washed with water. The organic phase is dried over $MgSO_4$ and the solvent is distilled off. After chromatographic purification of the residue (silica gel/chloroform:acetone=9:1), N-heptyl-N-methyl-5-heptyloxy-2,4-dibenzyloxy-cyclopentane-1-amine is obtained.

EXAMPLE 116

0.4 g of $NaBH_4$ is added to a mixture of 0.5 g of N-heptyl-N-methyl-2α,4α-dibenzyloxy-5α-(2-oxoheptyloxy)-cyclopentane-1β-amine (obtainable from 3α,5α-dibenzyloxy-2β-(N-heptyl-N-methylamino)-1α-cyclopentanol by reaction with 1-bromoheptan-2-one), 8 ml of methanol and 7 ml of tetrahydrofuran. This is stirred for 2 hours at room temperature and poured into 40 ml of $H_2O$. This is extracted three times with 20 ml amounts of $CHCl_3$, the organic phase is washed with water, and dried over $MgSO_4$. The solvent is distilled off. After chromatographic purification of the residue (silica gel/chloroform:acetone 9:1), N-heptyl-N-methyl-2α-4α-dibenzyloxy-5α-)2-hydroxyheptyloxy)-cyclopentane-1β-amine is obtained.

EXAMPLE 117

A mixture of 2 g of N-methyl-N-(6-cyano-hexyl)-2α,4α-dibenzyloxy-5α-heptyloxy-cyclopentane-1β-amine (obtainable from N-methyl-2α,4α-dibenzyloxy-5α-heptyloxy-cyclopentane-1β-amine by reaction with 1-iodo-6-cyanohexane in the presence of silver oxide), 20 ml of dioxane and 10 ml of concentrated hydrochloric acid is boiled for 2 hours. The solvent is distilled off and the residue taken up in water. This is neutralized by the addition of sodium bicarbonate; extracted exhaustively with chloroform; and the organic phase is dried over $Na_2SO_4$. The solvent is distilled off. After chromatographic purification of the residue (silica gel/chloroform:methanol=1:1), N-(5-hydroxycarbonyl-pentyl)-N-methyl-5α-heptyloxy-2α,4α-dihydroxy-cyclopentane-1β-amine is obtained.

IR: 1720 and 3350 cm$^{-1}$,
NMR: 0.95 (t) and 2.6 (s).

EXAMPLE 118

4 g of N-heptyl-N-methyl-2α,4α-dibenzyloxy-5α-heptyloxy-cyclopentane-1β-amine, dissolved in 50 ml of ethyl acetate, is hydrogenated in the presence of 2 g of 5% Pd-C catalyst at 30° and normal pressure. After the take up of the calculated amount of hydrogen, the medium is filtered. The solvent is distilled off and N-heptyl-N-methyl-2α,4α-dihydroxy-5α-heptyloxy-cyclopentane-1β-amine is obtained.

EXAMPLE 119

Dry HCl gas is passed for 6 hours through a solution of 0.3 g of N-(5-hydroxycarbonylpentyl)-N-methyl-2α,4α-dihydroxy-5α-heptyloxy-cyclopentane-1β-amine in 15 ml of dry ethanol at room temperature. The reaction mixture is then poured into 50 ml ice water. This is neutralized with sodium carbonate and extracted three times with 15 ml amounts of methylene chloride. The extract is dried over $MgSO_4$ the solvent is distilled off and as a residue, N-(5-ethoxycarbonyl-pentyl)-N-methyl-2α,4α-dihydroxy-5α-heptyloxy-cyclopentane-1β-amine is obtained;

IR: 1730 and 3400 cm$^{-1}$
NMR: 0.8 (t), 2.6 (s), 4.15 (2d).

EXAMPLE 120

To 0.2 g of N-(5-hydroxycarbonylpentyl)-N-methyl-2α,4α-dibenzyloxy-5α-heptyloxy-cyclopentane-1β-amine, dissolved in 10 ml of diethyl ether, ethereal diazomethane solution is dropped until the yellow color just remains. This is washed with 10 ml of 0.2% aqueous acetic acid and water and dried over $Na_2SO_4$. The solvent is distilled off and N-(5-methoxycarbonylpentyl)-N-methyl-2α,4α-dibenzyloxy-5α-heptyloxy-cyclopentane-1β-amine is obtained.

EXAMPLE 121

5.09 g of N-heptyl-2α,4α-dibenzyloxy-5α-heptyloxy-cyclopentane-1β-amine (obtainable from 3α,5α-dibenzyloxy-2β-heptylamino-1α-cyclopentanol by reaction with tert-butyloxycarbonyl azide analogously to Example 2; reaction of the reaction product with 1-iodo-heptane analogously to Example 3; and splitting off of the tert-butoxycarbonyl radical analogously to Example 4a with $CF_3COOH$) is heated with 1.5 g of methyl iodide and 40 ml of methanol in an autoclave for 4 hours at 100°. The solvent is distilled off after chromatographic purification of the residue (silica gel/chloroform- :acetone=9:1), N-heptyl-N-methyl-2α,4α-dibenzyloxy-5α-heptyloxy-cyclopentane-1β-amine is obtained;

NMR: 0.9 (t), 2.0 (t), 2.6 (s), 4.6 (m), 7.3 (s).

The following Examples concern mixtures of compounds of Formula I with carrier and adjuvant materials customary in pharmacy, which, in particular, can be used as medicaments:

EXAMPLE A: Tablets

A mixture consisting of 30 g of N-heptyl-N-methyl-5α-heptyloxy-2α,4α-dibenzyloxy-cyclopentane-1β-amine HCl, 50 g of lactose, 16 g of maize starch, 2 g of cellulose powder and 2 g of magnesium stearate is pressed into tablets in conventional fashion in such a manner that each tablet contains 10 mg of the active material.

Example B: Dragees

Tablets are pressed analogously to Example A and are subsequently coated with a coating consisting of sugar, maize starch, talc and tragacanth.

Example C: Ampoules 20 g of N-heptyl-N-methyl-5α-heptyloxy-2α,4α-dibenzyloxy-cyclopentane-1β-amine is dissolved in a mixture of 9.5 l of doubly distilled water and 0.5 l of ethylene glycol. This is sterily filtered and under sterile conditions, 5 ml amounts of the resultant solution are filled into ampoules which are subsequently heat sealed.

Tablets, dragees and ampoules are obtained analogously which contain one or more of the other active materials of Formula I.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclopentane-1-amine of the Formula

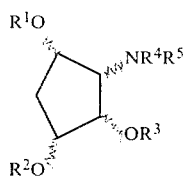

and the physiologically acceptable salts thereof, wherein $R^1$ and $R^2$ each is hydrogen or benzyl; $R^3$ is alkyl of 5-10 C-atoms or 2-hydroxyalkyl of 5-10 C-atoms; $R^4$ is hydrogen, methyl or ethyl, $R^5$ is alkyl of 5-10 C-atoms; and the wavy line ( ~~~ ) indicates that a bond can be in the α- or β-position.

2. The cyclopentane-1-amine of claim 1 wherein $R^1=R^2=$benzyl.

3. The cyclopentane-1-amine of claim 1 wherein $R^1=R^2=$H.

4. The cyclopentane-1-amine of claim 1 wherein $R^3=$unbranched alkyl of 5-10 C-atoms.

5. The cyclopentane-1-amine of claim 1 wherein $R^5=$unbranched alkyl of 5-10 C-atoms.

6. The cyclopentane-1-amine of claim 1 wherein $R^1=R^2=$benzyl, and $R^3=$unbranched alkyl of 5-10 C-atoms.

7. The cyclopentane-1-amine of claim 1 wherein $R^1=R^2=$benzyl, and $R^5=$unbranched alkyl of 5-10 C-atoms.

8. The cyclopentane-1-amine of claim 1 wherein $R^1=R^2=$benzyl, $R^3=$unbranched alkyl of 5-10 C-atoms, and $R^5=$unbranched alkyl of 5-10 C-atoms.

9. The cyclopentane-1-amine of claim 1 wherein $R^1=R^2=$benzyl, $R^3=$heptyl, and $R^5=$unbranched alkyl of 5-10 C-atoms.

10. The cyclopentane-1-amine of claim 1 wherein $R^1=R^2=$benzyl, $R^3=$heptyl and $R^5=$heptyl.

11. The cyclopentane-1-amine of claim 1 wherein $R^1=R^2=$benzyl, $R^3=$heptyl, $R^4=$methyl, and $R^5=$heptyl.

12. The cyclopentane-1-amine of claim 1 wherein $R^1=R^2=$H, $R^3=$heptyl, $R^4=$methyl, and $R^5=$heptyl.

13. The cyclopentane-1-amine of claim 1 having the formula

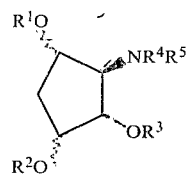

14. The cyclopentane-1-amine of claim 13 having the formula

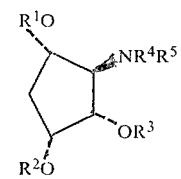

15. N-heptyl-N-methyl-5-heptyloxy-2,4-dibenzyloxy-cyclopentane-1-amine, a compound of claim 1.

16. N-heptyl-N-methyl-5-heptyloxy-2,4-dihydroxy-cyclopentane-1-amine, a compound of claim 1.

17. N-Methyl-5-heptyloxy-2,4-dibenzyloxy-cyclopentane-1-amine.

18. N-Methyl-5-(2-hydroxyheptyloxy-2,4-dibenzyloxy-cyclopentane-1-amine.

19. A pharmaceutical composition comprising an amount of a compound of claim 1 effective for inhibiting the aggregation or adhesion of thrombocytes and a pharmaceutically acceptable carrier.

20. A method of inhibiting aggregation or adhesion of thrombocytes in mammals which comprises administering an amount of a compound of claim 1 effective for such inhibition.

* * * * *